United States Patent [19]

Uno et al.

[11] Patent Number: 4,758,566
[45] Date of Patent: Jul. 19, 1988

[54] 2-(1-PIPERAZINYL)-4-SUBSTITUTED PHENYLQUINOLINE DERIVATIVES, PROCESSES FOR THE PREPARATION THEREOF, AND PHARMACEUTICAL COMPOSITION CONTAINING THE SAME

[75] Inventors: Hitoshi Uno, Takatsuki; Katsuhiko Hino, Ikoma; Toshiaki Kadokawa, Hirakata; Katsuyoshi Kawashima, Kobe, all of Japan

[73] Assignee: Dainippon Pharmaceutical Co., Ltd., Japan

[21] Appl. No.: 893,311

[22] PCT Filed: Nov. 27, 1985

[86] PCT No.: PCT/JP85/00654

§ 371 Date: Jul. 28, 1986

§ 102(e) Date: Jul. 28, 1986

[87] PCT Pub. No.: WO86/03198

PCT Pub. Date: Jun. 5, 1986

[30] Foreign Application Priority Data

Nov. 27, 1984 [JP] Japan ................. 59-251317

[51] Int. Cl.$^4$ .............. A61K 31/495; C07D 401/02
[52] U.S. Cl. ..................... 514/254; 544/363
[58] Field of Search ................ 544/363; 514/254

[56] References Cited

U.S. PATENT DOCUMENTS

| 3,542,785 | 11/1970 | Carney | 544/363 |
| 3,668,207 | 6/1972 | Carney | 544/363 |
| 3,957,791 | 5/1976 | Simpson | 544/363 |
| 3,983,121 | 9/1976 | Murthi et al. | 544/363 |
| 4,237,135 | 12/1980 | Uno et al. | 544/363 |

OTHER PUBLICATIONS

Carney, "Chemical Abstracts", vol. 74, 1971, col. 125470n.
Carney, "Chemical Abstracts", vol. 77, 1972, col. 126452g.
Gast, et al., "Chemical Abstracts", vol. 87, 1977, col. 87:151994z.
Uno, et al., "Chemical Abstracts", vol. 92, 1980, col. 92:41784b.
Karasawa, et al., "Chemical Abstracts", vol. 93, 1980, col. 93:215385k.
Hino et al., "Chemical Abstracts", vol. 94, 1981, col. 94:30538q.
Kadokawa, et al., "Chemical Abstracts", vol. 102, 1985, col. 102:84423a.
Alhaider, et al., "Chemical Abstracts", vol. 103, 1985, col. 103:160473e.
Chem. Phar. Bull., 28(9), 2618-2622, (1980).

Primary Examiner—Glennon H. Hollrah
Assistant Examiner—James H. Turnipseed
Attorney, Agent, or Firm—Scully, Scott, Murphy & Presser

[57] ABSTRACT

Compounds of the formula:

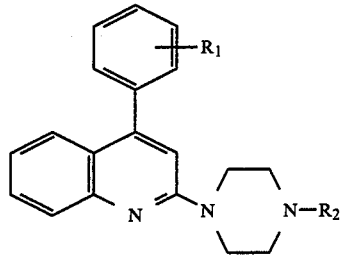

wherein $R_1$ represents fluorine atom at the para position, chlorine atom at the para position, methyl group at the para position or trifluoromethyl group at the para or meta position; and $R_2$ represents hydrogen atom, methyl group, ethyl group, 2-hydroxyethyl group or 3-hydroxypropyl group, provided that $R_2$ represents ethyl group, 2-hydroxyethyl group or 3-hydroxypropyl group when $R_1$ represents fluorine atom at the para position, methyl group at the para position or trifluoromethyl group at the para position, and a pharmaceutically acceptable salt therof, process for the preparation thereof, and pharmaceutical composition containing the same. The compounds and pharmaceutically acceptable salts thereof show excellent cytoprotective effect and useful for prophylaxis and treatment of peptic ulcer and inflammatory gastrointestinal diseases.

6 Claims, No Drawings

2-(1-PIPERAZINYL)-4-SUBSTITUTED PHENYLQUINOLINE DERIVATIVES, PROCESSES FOR THE PREPARATION THEREOF, AND PHARMACEUTICAL COMPOSITION CONTAINING THE SAME

TECHNICAL FIELD

The present invention relates to novel and useful 2-(1-piperazinyl)-4-substituted phenylquinoline derivatives having cytoprotective effect, processes of the preparation thereof, and a pharmaceutical composition containing the same.

BACKGROUND ART

The leading view as to etiology of peptic ulcer is that it is induced by imbalance of the aggressive factor such as hydrochloric acid or pepsin and the defensive factor such as mucosal resistance. Type 2 histamine ($H_2$) receptor antagonists such as cimetidine which has widely been used for the treatment of peptic ulcer depress the aggressive factor and thereby shows high healing effect on peptic ulcer, but on the other hand, these agents cause decrease of gastric mucosal resistance when administered continuously, and it is assumed that it is one of the reasons of recurrence of ulcer. Accordingly, it is very desirable to develop an antiulcer drug having properties well balanced in both of depression of the aggressive factor and increase of the defensive factor. Besides, in the aged patients, there is comparatively frequently observed the peptic ulcer with low gastric acidity, and hence, it is also desired to develop a drug having an activity of specifically increasing the defensive factor.

By the way, there are known some 2-(1-piperazinyl)-4-phenylquinoline derivatives which have some pharmacological activities. These are summarized below.

It is disclosed in U.S. Pat. No. 4,237,135 that 2-(4-ethyl-1-piperazinyl)-4-phenylquinoline and salts thereof have an antireserpine activity, inhibitory effect on spontaneous locomotor activity, and the like and are useful as an antidepressant with neuroleptic-like properties such as inhibition of central nervous system and further that the compounds have also antitremorine activity.

It is disclosed in U.S. Pat. Nos. 3,542,785 and 3,668,207 that 2-amino-4-arylquinoline derivatives including 6-chloro-2-(4-methyl-1-piperazinyl)-4-phenylquinoline have antiinflammatory and diuretic activities.

It is disclosed in Chem. Pharm. Bull., 28, 2618 (1980) that the pharmacological activities of the compounds as disclosed in the above U.S. Pat. Nos. 4,237,135, 3,542,785 and 3,668,207 and related compounds were evaluated from the viewpoint of screening antidepressant having also neuroleptic-like properties such as inhibition of central nervous system. Besides, it is also reported that some of these compounds have antitremorine activity.

The present inventors have studied as to pharmacological activities of 2-(1-piperazinyl)-4-phenylquinoline derivatives, and in the studies, they have found that the compounds having a specific substituent on the phenyl ring at the 4-position have cytoprotective effect and are useful as an antiulcer agent and a therapeutic agent for inflammatory gastrointestinal diseases, and then, the present invention has been accomplished.

DISCLOSURE OF THE INVENTION

The present invention provides compounds of the formula (I):

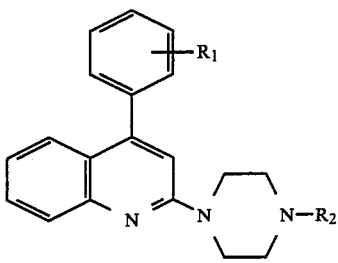

wherein $R_1$ represents fluorine atom at the para position, chlorine atom at the para position, methyl group at the para position or trifluoromethyl group at the para or meta position: and $R_2$ represents hydrogen atom, methyl group, ethyl group, 2-hydroxyethyl group or 3-hydroxypropyl group, provided that $R_2$ represents ethyl group, 2-hydroxyethyl group or 3-hydroxypropyl group when $R_1$ represents fluorine atom at the para position, methyl group at the para position or trifluoromethyl group at the para position, and a pharmaceutically acceptable salt thereof, a process of the preparation of the compounds, and a pharmaceutical composition containing the compounds as an active ingredient.

The pharmaceutically acceptable salts of the compounds (I) include, for example, inorganic acid addition salts (e.g. hydrochloride, hydrobromide, hydroiodide, sulfate, phosphate, etc.) and organic acid addition salts (e.g. citrate, maleate, fumarate, tartrate, benzoate, lactate, methanesulfonate, etc.). The compounds (I) and salts thereof may optionally be present in the form of a hydrate, and these hydrates are also included in the present invention.

The compounds of the present invention may be divided into the following two groups in view of the pharmacological properties. The first group is the compounds having properties well balanced in the gastro-cytoprotective effect (increase of defensive factor) and inhibitory effect on gastric acid secretion (depression of aggressive factor). These compounds have very desirable profile as an antiulcer agent. The second group is the compounds having no inhibitory effect on gastric acid secretion but having potent gastro-cytoprotective effect and hence these are particularly useful for the treatment of peptic ulcer patients with low gastric acidity. By the way, the compounds of the present invention show comparatively weak or no antireserpine activity.

Examples of the compounds of the first group are the following compounds and pharmaceutically acceptable salts thereof:

2-[4-(2-hydroxyethyl)-1-piperazinyl]-4-(4-fluorophenyl)quinoline,

2-[4-(3-hydroxypropyl)-1-piperazinyl]-4-(4-fluorophenyl)quinoline, 2-(1-piperazinyl)-4-(4-chlorophenyl)quinoline, 2-(4-ethyl-1-piperazinyl)-4-(4-chlorophenyl)quinoline, 2-[4-(2-hydroxyethyl)-1-piperazinyl]-4-(4-methylphenyl)quinoline, and 2-[4-(2-hydroxyethyl)-1-piperazinyl]-4-(4-trifluoromethylphenyl)quinoline.

Examples of the compounds of the second group are the following compounds and pharmaceutically acceptable salts thereof:

2-[4-(2-hydroxyethyl)-1-piperazinyl]-4-(4-chlorophenyl)quinoline,
2-(1-piperazinyl)-4-(3-trifluoromethylphenyl)quinoline,
2-(4-ethyl-1-piperazinyl)-4-(3-trifluoromethylphenyl)quinoline, and
2-[4-(2-hydroxyethyl)-1-piperazinyl]-4-(3-trifluoromethylphenyl)quinoline.

The compounds of the present invention can be prepared, for example, by the following processes.

Process (a)

The compounds of the formula (I) can be prepared by reacting a compound of the formula (II):

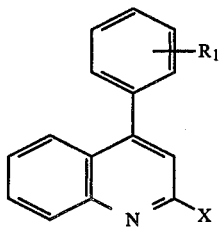

(II)

wherein X represents a leaving atom or group, and $R_1$ is as defined above, with a piperazine compound of the formula (III):

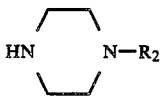

(III)

wherein $R_2$ is as defined above.

The leaving atom or group represented by X in the formula (II) denotes any atom or group which can leave off in the form of HX under the reaction conditions together with hydrogen atom bonded to the nitrogen atom at the 4-position of the piperazine compound (III). Examples of the leaving atom or group are a halogen atom such as chlorine or bromine, a lower alkylthio group such as methylthio or ethylthio, a lower alkylsulfinyl group such as methanesulfinyl or ethanesulfinyl, a lower alkylsulfonyl group such as methanesulfonyl or ethanesulfonyl, a lower alkylsulfonyloxy group such as methanesulfonyloxy or ethanesulfonyloxy, and an arylsulfonyloxy group such as benzenesulfonyloxy, p-toluenesulfonyloxy or m-nitrobenzenesulfonyloxy.

The reaction of the compound (II) and the piperazine compound (III) is carried out in a suitable solvent or without using any solvent. Suitable examples of the solvent are aromatic hydrocarbons (e.g. toluene, xylene), ketones (e.g. methyl ethyl ketone), ethers (e.g. dioxane, diglyme), alcohols (e.g. ethanol, isopropyl alcohol), dimethylformamide, and dimethyl sulfoxide. These solvents may be used alone or in combination of two or more thereof. The reaction is preferably carried out in the presence of a base, but the compound (III) may be used in an excess amount to serve as the base. Suitable examples of the base are alkali metal carbonates (e.g. sodium carbonate, potassium carbonate), alkali metal bicarbonates (e.g. sodium bicarbonate, potassium bicarbonate), and tertiary amines (e.g. triethylamine). When the piperazine compound (III) exists in the form of a hydrate, it can be used as it is. The reaction is usually carried out at a temperature of from about 20° C. to about 200° C., preferably of from about 70° C. to about 150° C.

The starting compounds (II) can be prepared, for example, according to the process as disclosed in U.S. Pat. No. 3,668,207 or Chem. Pharm. Bull., 28, 2618 (1980).

Process (b)

The compound of the formula (I) in which $R_2$ is methyl group, ethyl group, 2-hydroxyethyl group or 3-hydroxypropyl group can be prepared by reacting a compound of the formula (I'):

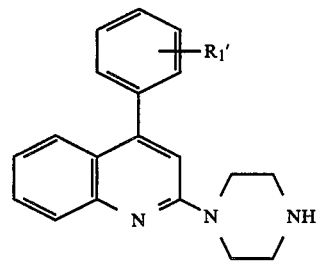

(I')

wherein $R_1$ is as defined above, with a compound of the formula (IV):

$R_2'—Y$     (IV)

wherein Y represents a residue of a reactive ester of an alcohol and $R_2'$ represents methyl group, ethyl group, 2-hydroxyethyl group or 3-hydroxypropyl group.

In the formula (IV), the residue of a reactive ester of an alcohol represented by Y includes, for example, a halogen atom such as chlorine, bromine or iodine, a lower alkoxysulfonyloxy such as ethoxysulfonyloxy, an lower alkylsulfonyloxy such as methanesulfonyloxy or ethanesulfonyloxy, an arylsulfonyloxy such as benzenesulfonyloxy, p-toluenesulfonyloxy or m-nitrobenzenesulfonyloxy.

The reaction of the compound (I') and the compound (IV) is carried out in a suitable solvent or without using any solvent. Suitable examples of the solvent are aromatic hydrocarbons (e.g. benzene, toluene, xylene), ketones (e.g. methyl ethyl ketone), ethers (e.g. dioxane), alcohols (e.g. methanol, ethanol, isopropyl alcohol), and dimethylformamide. These solvents may be used alone or in combination of two or more thereof. The reaction is preferably carried out in the presence of a base. Suitable examples of the base are the same as described above as to the process (a). The reaction is usually carried out at a temperature of from about 20° C. to about 200° C., preferably of from about 50° C. to about 150° C.

Process (c)

The compound of the formula (I) in which $R_2$ is 2-hydroxyethyl group can be prepared by reacting a compound of the above formula (I') with ethylene oxide.

The reaction is carried out in a suitable solvent or without using any solvent. Suitable examples of the solvent are the same as described above as to the process (b). The reaction temperature is usually in the range of from about 20° C. to about 200° C., preferably from about 50° C. to about 150° C. The reaction may optionally be carried out under pressure.

The starting compounds (I') used in the processes (b) and (c) can be prepared, for example, by reacting the compound (II) with piperazine according to the process (a). In the reaction, piperazine may be used in the form of a hydrate.

The compounds prepared by the above processes can be isolated and purified in a usual manner.

The compound (I) may be obtained in the form of a free base, salt or hydrate depending on the kinds of the starting compounds, reaction and treating conditions, and the like. The salt can be converted into a free base by treating it with a base such as an alkali metal hydroxide in a usual manner. On the other hand, the free base may be converted into a salt by treating it with various acids in a usual manner. For instance, when a compound of the formula (I) is reacted with an appropriate acid in a solvent and the reaction product is purified by recrystallization or reprecipitation, there is obtained a salt of the compound (I). The solvent includes, for example, ethyl acetate, methanol, ethanol, isopropyl alcohol, water, and the like. The acid is usually used in an amount of one to about three moles to one mole of the compound (I). The reaction temperature is usually in the range of from about 10° C. to about 80° C.

The pharmacological activities of the compounds of the present invention are illustrated by the following experiments, which were carried out as to the representative compounds of the present invention. Cimetidine and imipramine hydrochloride which are commercially available antiulcer agent and antidepressant agent, respectively, were used as reference compounds.

The compounds of the present invention used in the experiments are as follows:

A: 2-[4-(2-hydroxyethyl)-1-piperazinyl]-4-(4-fluorophenyl)quinoline dihydrochloride, B: 2-[4-(3-hydroxypropyl)-1-piperazinyl]-4-(4-fluorophenyl)quinoline dimaleate, C: 2-(1-piperazinyl)-4-(4-chlorophenyl)quinoline maleate, D: 2-(4-ethyl-1-piperazinyl)-4-(4-chlorophenyl)quinoline dimaleate, E: 2-[4-(2-hydroxyethyl)-1-piperazinyl]-4-(4-methylphenyl)quinoline dimaleate, F: 2-[4-(2-hydroxyethyl)-1-piperazinyl]-4-(4-trifluoromethylphenyl)quinoline dimaleate, G: 2-[4-(2-hydroxyethyl)-1-piperazinyl]-4-(4-chlorophenyl)quinoline dimaleate, H: 2-(1-piperazinyl)-4-(3-trifluoromethylphenyl)quinoline dimaleate, I: 2-(4-ethyl-1-piperazinyl)-4-(3-trifluoromethylphenyl)quinoline dimaleate, and J: 2-[4-(2-hydroxyethyl)-1-piperazinyl]-4-(3-trifluoromethylphenyl)quinoline dimaleate.

Test 1

Effect on the ulceration induced by ethanol in rats (gastric cytoprotection activity)

This test was carried out according to the method of Robert [cf. Gastroenterology, 77, 433 (1979)].

Male Wistar rats weighing 190 g to 200 g were fasted for 24 hours and then given orally 1 ml of absolute ethanol. After 1 hour, the animals were sacrificed under ether anesthesia, and the stomachs were removed and cut along the greater curvature. The length (mm) of each lesion in the glandular portion was measured using a dissecting microscope ($\times 12$). The sum of the length (mm) of each lesion in a stomach was indicated as an ulcer index. The inhibitory rate was determined by comparing the ulcer index in drug-treated groups with that in control group. Test compounds were administered orally 30 minutes before the administration of ethanol. In the control group, a vehicle (a 0.5% tragacanth solution) was administered orally. The results are shown in Table 1.

TABLE 1

| Test compound | Dose (mg/kg, p.o.) | Number of animals | Ulcer index (mm) | Inhibitory rate (%) |
|---|---|---|---|---|
| Control | — | 10 | 47.8 ± 7.6 | — |
| A | 5 | 10 | 31.6 ± 11.3 | 33.9 |
|  | 10 | 10 | 9.8 ± 2.9** | 79.5 |
|  | 20 | 10 | 9.2 ± 4.1** | 80.8 |
| Control | — | 5 | 71.0 ± 13.9 | — |
| B | 10 | 5 | 21.9 ± 12.1* | 69.2 |
| Control | — | 5 | 35.7 ± 8.7 | — |
| C | 10 | 5 | 4.5 ± 3.7* | 87.4 |
| Control | — | 5 | 45.2 ± 9.6 | — |
| D | 10 | 5 | 8.6 ± 4.5** | 89.0 |
| G | 10 | 5 | 10.8 ± 6.3* | 76.1 |
| H | 10 | 5 | 7.1 ± 1.9* | 84.3 |
| I | 10 | 5 | 16.5 ± 3.9* | 63.5 |
| Control | — | 5 | 33.7 ± 7.4 | — |
| E | 10 | 5 | 12.0 ± 2.3* | 64.4 |
| Control | — | 5 | 52.4 ± 16.2 | — |
| F | 10 | 5 | 6.7 ± 1.8* | 87.2 |
| Control | — | 5 | 35.7 ± 8.7 | — |
| J | 10 | 5 | 9.0 ± 4.2* | 74.8 |
| Control | — | 5 | 31.9 ± 3.4 | — |
| Cimetidine | 100 | 5 | 23.9 ± 8.2 | 25.1 |

*$p < 0.05$
**$p < 0.01$

As shown in Table 1, compounds A to J of the present invention showed significant protective effect at a dose of 10 mg/kg on the ethanol-induced ulceration. On the other hand, cimetidine did not exhibit any significant protective effect even at a dose of 100 mg/kg.

Test 2

Effect on the ulceration induced by exposure to stress (restraint and water immersion) in rats The effect evaluated by this test is considered to be fairly well correlative to inhibitory effect on gastric acid secretion.

Male Wistar rats weighing about 200 g were used in groups of 5 animals each. According to the method of Takagi et al. [cf. Japan. J. Pharmacol., 18, 9 (1968)], the animals were placed in individual cages which served to immobilize them therein and then immersed in a water bath of 23° C. to a height of their breast in order to give stress. After 20 hours, the animals were taken out from the water bath and sacrificed under ether anesthesia, and the stomachs were removed. The stomach was inflated with 13 ml of physiological saline and placed in a 5% formalin solution for 5 minutes. After washing with physiological saline, the stomach was cut along the greater curvature and the length (mm) of each lesion in the glandular portion was measured using a dissecting microscope ($\times 12$). The sum of the length (mm) of each lesion in a stomach was indicated as an ulcer index. The inhibitory rate was determined by comparing the ulcer index in drug-treated groups with that in control group. Test compounds were administered orally 30 minutes before the immersion. In the control group, a vehicle (a 0.5% tragacanth solution) was administered orally. The results are shown in Table 2.

TABLE 2

| Test compound | Dose (mg/kg, p.o.) | Ulcer index (mm) | Inhibitory rate (%) |
|---|---|---|---|
| Control | — | 24.0 ± 2.6 | — |
| A | 10 | 7.4 ± 3.6** | 69.2 |
| Control | — | 19.3 ± 3.4 | — |
| B | 10 | 7.4 ± 1.2* | 61.7 |
| Control | — | 24.7 ± 3.2 | — |
| C | 10 | 8.5 ± 2.9** | 65.6 |
| Control | — | 29.1 ± 1.6 | — |
| D | 10 | 13.4 ± 2.1** | 54.0 |
| G | 10 | 18.5 ± 6.9 | 36.4 |
| Control | — | 38.9 ± 6.6 | — |
| E | 10 | 11.8 ± 4.6** | 69.7 |
| Control | — | 33.9 ± 3.9 | — |
| F | 10 | 19.8 ± 2.0* | 41.6 |
| I | 10 | 27.1 ± 2.2 | 20.1 |
| J | 10 | 34.8 ± 3.9 | −2.7 |
| Control | — | 25.8 ± 2.9 | — |
| H | 10 | 24.7 ± 3.6 | 4.3 |
| Control | — | 24.8 ± 3.8 | — |
| Cimetidine | 20 | 15.1 ± 2.9 | 39.1 |

*$p < 0.05$
**$p < 0.01$

As shown in Table 2, compounds A to F of the present invention showed significant preventive effect at a dose of 10 mg/kg on the stress-induced ulceration. On the other hand, compounds G to J and cimetidine did not exhibit any significant effect at a dose of 10 mg/kg and 20 mg/kg, respectively.

Test 3

Effect on the ulceration induced by pylorus-ligation (Shay ulcer) in rats

Male Wistar rats weighing about 190 g were fasted for 48 hours before experiment. The portion between pylorus and duodenum of each rat was ligated under ether anesthesia according to the method of Shay et al. [Gastroenterology, 5, 43 (1945)]. Each of the animals was then allowed to stand abstained from food and water in a cage. After 18 hours, the animals were sacrificed under ether anesthesia, and the stomachs were removed and cut along the greater curvature. The state of ulceration was macroscopically observed and degree of ulceration was estimated according to the following ulcer indices of 0 to 5:
0: no lesion
1: hemorrhage or erosion
2: one to four small ulcers of a diameter of less than 5 mm
3: five or more small ulcers, or one marked ulcer of a diameter of 5 mm or more
4: two or more marked ulcers
5: perforated ulcer The inhibitory rate was determined by comparing the ulcer index in drug-treated groups with that in the control group. In addition, $ED_{50}$, i.e. the dose required to inhibit ulcer index by 50%, was determined by the usual graphic method. Test compounds were administered orally 30 minutes before the ligation. In the control group, a vehicle (a 0.5% tragacanth solution) was administered orally. The results are shown in Table 3.

TABLE 3

| Test Compound | Dose (mg/kg, p.o.) | Number of animals | Ulcer index (mm) | Inhibitory rate (%) | $ED_{50}$ (mg/kg, p.o.) |
|---|---|---|---|---|---|
| Control | — | 5 | 3.6 ± 0.2 | — | |
| A | 10 | 5 | 2.4 ± 0.4* | 33.3 | |
| | 20 | 5 | 2.0 ± 0.8 | 44.4 | 26.5 |
| | 50 | 5 | 1.4 ± 0.2** | 61.1 | |
| | 100 | 5 | 1.2 ± 0.2** | 66.7 | |
| Control | — | 9 | 3.3 ± 0.4 | — | |
| Cimetidine | 50 | 9 | 3.3 ± 0.3 | 0 | |
| | 100 | 10 | 3.0 ± 0.5 | 9.1 | 253 |
| | 200 | 9 | 1.9 ± 0.4* | 42.4 | |
| | 500 | 5 | 0.8 ± 0.2** | 75.8 | |

*$p < 0.05$
**$p < 0.01$

As shown in Table 3, compound A of the present invention was about 10 times more potent than cimetidine in preventive effect on Shay ulcer.

Test 4

Antireserpine activity (antagonistic effect on hypothermia induced by reserpine)

This test was carried out according to the method of Askew [cf. Life Sci., 2, 725 (1963)].

Male ddY mice weighing 22 g to 27 g were used in groups of 5 animals each. Test compounds were administered orally to the animals, and immediately 5 mg/kg of reserpine was injected intraperitoneally. Rectal temperature of each mouse was measured 4 hours later with a thermistor (Shibaura Electric, BMG III-130). The inhibitory rate was determined by comparing the fall of rectal temperature in drug-treated groups with that in control group. In the control group, a vehicle (a 0.5% tragacanth solution) was administered orally. The results are shown in Table 4.

TABLE 4

| Test compound | Dose (mg/kg, p.o.) | Inhibitory rate (%) |
|---|---|---|
| A | 50 | 20.6 |
| | 100 | 65.5 |
| B | 100 | 59.4 |
| C | 100 | 64.3 |
| D | 100 | 45.2 |
| E | 100 | 51.3 |
| Imipramine hydrochloride | 10 | 29.5 |
| | 30 | 69.3 |
| | 100 | 94.5 |

As shown in Table 4, the potency of antireserpine activity of compounds A to E of the present invention was one-third or less compared to that of imipramine hydrochloride. Compounds F to J did not show any antireserpine activity at a dose of 100 mg/kg.

It is evident from the results of Tests 1 to 4 that:

(1) compounds A to F show significant preventive effects on the ethanol-induced and stress-induced ulcerations, and hence these compounds increase the defensive factor, thereby enhancing mucosal resistance, and also depress the aggressive factor (gastric acid secretion);

(2) compounds G to J do not show any significant activity against the stress-induced ulceration at a dose of 10 mg/kg, but significant protective activity against the ethanol-induced ulceration at the same dose, and hence these compounds do not affect the aggressive factor but increase the defensive factor, thereby enhancing mucosal resistance; and (3) the antireserpine activity of compounds A to J is relatively weak or devoid.

Test 5

Acute toxicity

Male ddY mice weighing 20 g to 25 g were used in groups of 10 animals each. Test compounds, dissolved or suspended in a 0.5% tragacanth solution, were orally administered at a prescribed dose to the animals. The mortality was observed for 7 days after the administration.

As shown in Table 5, the death of mouse was not observed by administration of 250 mg/kg of compound A. Therefore, it is clear that the toxic dose of the compound is far greater than the dose required to exhibit antiulcer activity. The toxicity of compounds B to J was as weak as that of compound A.

TABLE 5

| Test compound | Dose (mg/kg, p.o.) | Number of dead animals/ number of used animals |
|---|---|---|
| A | 250 | 0/10 |
|  | 500 | 2/10 |
|  | 1000 | 5/10 |

As is clear from the above explanation, the compounds of the formula (I) and pharmaceutically acceptable salts thereof have excellent cytoprotective effect with less toxicity, and hence, can be used as an antiulcer agent for the prophylaxis and treatment of peptic ulcer in mammals including human. The compounds of the present invention can also be used as a therapeutic agent for the prophylaxis and treatment of inflammatory gastrointestinal diseases such as gastritis and duodenitis.

The compounds of the formula (I) and pharmaceutically acceptable salts thereof can be administered by oral, parenteral or intrarectal route, preferably by oral route. The clinical dose of the compounds (I) and pharmaceutically acceptable salts thereof may vary according to the kinds of the compounds, administration routes, severity of disease, age of patients, or the like, but is usually in the range of 0.1 to 20 mg per kg of body weight per day, preferably 0.2 to 10 mg per kg of body weight per day, in human. The dose may be divided and administered in two to several times per day.

The compounds of the formula (I) and pharmaceutically acceptable salts thereof are usually administered to patients in the form of a pharmaceutical composition which contains a non-toxic and effective amount of the compounds. The pharmaceutical composition is usually prepared by admixing the active compounds (I) or their salts with conventional pharmaceutically acceptable carrier materials which are unreactive with the active compounds (I) or their salts. Suitable examples of the carrier materials are lactose, glucose, mannitol, dextrin, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, propylene glycol, water, or the like.

The pharmaceutical composition may be in the dosage form of tablets, capsules, granules, fine granules, powders, syrups, suspension, injections, suppositories, or the like. These preparations may be prepared by conventional methods. Liquid preparations may be prepared by dissolving or suspending the active compounds in water or other suitable vehicles, when used. Tablets, granules and fine granules may be coated in a conventioanl manner. For preparing injection preparation, a pharmaceutically acceptable salt of the compound of the formula (I) is dissolved in water, or it may optionally be dissolved in physiological saline or glucose solution. And further pH adjusting agents and preservatives may also optionally be added.

The pharmaceutical composition may contain as the active ingredient the compound of the formula (I) or its pharmaceutically acceptable salt in the ratio of 0.5% by weight or more, preferably 1 to 70% by weight, based upon the whole weight of the composition. The composition may further contain one or more other therapeutically active compounds.

BEST MODE FOR CARRYING OUT THE INVENTION

The present invention is illustrated by the following Examples and Reference Examples, but should not be construed to be limited thereto. The identification of the compounds is carried out by elementary analysis, mass spectrum, IR spectrum, NMR spectrum, and the like.

EXAMPLE 1

Preparation of 2-[4-(2-hydroxyethyl)-1-piperazinyl]-4-(4-fluorophenyl)quinoline dihydrochloride A mixture of 16 g of 2-chloro-4-(4-fluorophenyl)-quinoline and 25.4 g of 1-(2-hydroxyethyl)piperazine is stirred at 130° C. for 3 hours. After cooling, water is added and the resulting mixture is extracted with ethyl acetate. The organic layer is dried over anhydrous sodium sulfate and concentrated under reduced pressure. The residue is chromatographed on silica gel (150 g) with chloroform - methanol (100 : 1). The eluates pooled are concentrated to give an oily residue, which is treated with ethanolic hydrogen chloride to afford the hydrochloride. Recrystallization from ethanol - ethyl acetate gives 16.7 g of the title compound, m.p. 210°–218° C.

EXAMPLE 2

Preparation of 2-(4-ethyl-1-piperazinyl)-4-(4-chlorophenyl)quinoline dimaleate

A mixture of 1.36 g of 2-chloro-4-(4-chlorophenyl)-quinoline and 1.7 g of 1-ethylpiperazine is stirred at 130° C. for 2 hours. After cooling, water is added and the resulting mixture is extracted with ethyl acetate. The organic layer is dried over anhydrous sodium sulfate and concentrated under reduced pressure. The residue is chromatographed on silica gel (18 g) with chloroform. The first eluate is discarded, and the subsequent eluates are pooled and concentrated. The residue is treated with a solution of maleic acid in ethyl acetate to afford the maleate. Recrystallization from water - methanol - ethyl acetate gives 1.9 g of the title compound, m.p. 187°–189° C.

EXAMPLE 3

Preparation of 2-(1-piperazinyl)-4-(3-trifluoromethylphenyl)quinoline dimaleate

A mixture of 1.2 g of 2-chloro-4-(3-trifluoromethylphenyl)quinoline, 1.3 g of anhydrous piperazine and 1 ml of toluene is heated under reflux for 3 hours. After cooling, water is added and the resulting mixture is extracted with ethyl acetate. The organic layer is dried over anhydrous sodium sulfate and concentrated under reduced pressure. The residue is chromatographed on silica gel (10 g) with chloroform. The first eluate is discarded, and the subsequent eluates are pooled and concentrated. The residue is treated with a solution of maleic acid in ethyl acetate to afford the maleate. Recrystallization from methanol - ethyl acetate gives 1.5 g of the title compound, m.p. 159-°160° C.

EXAMPLE 4

Preparation of 2-[4-(2-hydroxyethyl)-1-piperazinyl]-4-(4-fluorophenyl)quinoline dihydrochloride A mixture of 1.23 g of 2-(1-piperazinyl)-4-(4-fluorophenyl)quinoline, 0.9 g of 2-bromoethanol and 1.1 g of potassium carbonate in 15 ml of dimethylformamide is stirred at 100° C. for 3 hours. After cooling, ice-water is added and the resulting mixture is extracted with ethyl acetate. The organic layer is dried over anhydrous sodium sulfate and concentrated under reduced pressure. The residue is treated in substantially the same manner as in Example 1 to give 1.2 g of the title compound, m.p. 210°-218° C. (recrystallized from ethanol - ethyl acetate).

EXAMPLE 5

Preparation of 2-(4-ethyl-1-piperazinyl)-4-(4-chlorophenyl)quinoline dimaleate

A mixture of 1.41 g of 2-(1-piperazinyl)-4-(4-chlorophenyl)quinoline, 0.8 g of ethyl iodide and 0.5 g of sodium carbonate in 20 ml of methyl ethyl ketone is refluxed with stirring for 8 hours. The reaction mixture is concentrated under reduced pressure and water is added. The resulting mixture is extracted with ethyl acetate, and the organic layer is dried over anhydrous sodium sulfate and concentrated. The residue is treated in substantially the same manner as in Example 2 to give 1.82 g of the title compound, m.p. 187°-189° C. (recrystallized from water - methanol - ethyl acetate).

EXAMPLE 6

Preparation of 2-[4-(3-hydroxypropyl)-1-piperazinyl]-4-(4-fluorophenyl)quinoline dimaleate A mixture of 1.23 g of 2-(1-piperazinyl)-4-(4-fluorophenyl)quinoline, 0.42 g of sodium carbonate and 0.8 g of 3-chloropropyl alcohol in 10 ml of methyl ethyl ketone is heated under reflux for 20 hours. After cooling, water is added and the resulting mixture is extracted with ethyl acetate. The organic layer is dried over anhydrous sodium sulfate and concentrated under reduced pressure. The residue is chromatographed on silica gel (15 g) with chloroform - methanol (100:1). The eluates pooled are concentrated to give an oily residue, which is treated with a solution of maleic acid in ethyl acetate to afford the maleate. Recrystallization from methanol - ethyl acetate gives 1.6 g of the title compound, m.p. 175°-177° C.

EXAMPLE 7

Preparation of 2-[4-(2-hydroxyethyl)-1-piperazinyl]-4-(4-fluorophenyl)quinoline dihydrochloride A mixture of 1.23 g of 2-(1-piperazinyl)-4-(4-fluorophenyl)quinoline, 0.6 g of ethylene oxide and 30 ml of methanol is heated at 50° C. for 6 hours in a sealed tube. The solvent is distilled off and the residue is chromatographed on silica gel (15 g) with chloroform. Thereafter, substantially the same procedures as in Example 1 are carried out to give 0.8 g of the title compound, m.p. 210-°218° C. (recrystallized from ethanol - ethyl acetate).

EXAMPLES 8 to 15

The following compounds are prepared in substantially the same manner as in Examples 1 to 7 using the corresponding starting materials and recrystallized from the solvent designated in parentheses after the indication of melting points:

2-(4-ethyl-1-piperazinyl)-4-(4-fluorophenyl)quinoline dihydrochloride monohydrate, m.p. 230°-235° C. (ethanol);

2-(1-piperazinyl)-4-(4-chlorophenyl)quinoline maleate, m.p. 185°-186° C. (water - methanol - ethyl acetate);

2-[4-(2-hydroxyethyl)-1-piperazinyl]-4-(4-chlorophenyl)quinoline dimaleate, m.p. 178°-180° C. (water - methanol - ethyl acetate);

2-[4-(2-hydroxyethyl)-1-piperazinyl]-4-(4-methylphenyl)quinoline dimaleate, m.p. 169°-170° C. (methanol - ethyl acetate);

2-(4-ethyl-1-piperazinyl)-4-(4-trifluoromethylphenyl)quinoline dimaleate, m.p. 182°-183° C. (water - methanol - ethyl acetate);

2-[4-(2-hydroxyethyl)-1-piperazinyl]-4-(4-trifluoromethylphenyl)quinoline dimaleate, m.p. 174°-175° C. (water - methanol - ethyl acetate);

2-(4-ethyl-1-piperazinyl)-4-(3-trifluoromethylphenyl)quinoline dimaleate, m.p. 168°-169° C. (methanol - isopropyl alcohol); and 2-[4-(2-hydroxyethyl)-1-piperazinyl]-4-(3-trifluoromethylphenyl)quinoline dimaleate, m.p. 143°-144° C. (methanol - ethyl acetate).

The starting materials used in Examples 1 to 15 can be prepared by the method described in the following Reference Examples.

REFERENCE EXAMPLE 1

Preparation of 4-(4-fluorophenyl)carbostyril

To a refluxed solution of 40 g of 2-(4-fluorobenzoyl)acetanilide in 300 ml of ethanol, a sodium ethylate solution, prepared from 9.13 g of sodium and 150 ml of ethanol, is added dropwise over a period of 2 hours. The reaction mixture is refluxed for 20 minutes, allowed to cool and poured onto ice-water. The precipitate is collected, dried and recrystallized from chloroform - diethyl ether to give 31.3 g of the title compound, m.p. 247°-248° C.

REFERENCE EXAMPLES 2 to 5

The following compounds are prepared in substantially the same manner as in Reference Example 1 using the corresponding starting materials and recrystallized from the solvent designated in parentheses after the indication of melting points:

4-(4-chlorophenyl)carbostyril, m.p. 250°–251° C. (chloroform - diethyl ether);

4-(4-methylphenyl)carbostyril, m.p. 248°–249° C. (chloroform - ethyl acetate);

4-(4-trifluoromethylphenyl)carbostyril, m.p. 254° C. (chloroform - ethyl acetate); and 4-(3-trifluoromethylphenyl)carbostyril, m.p. 237° C. (chloroform - ethyl acetate).

REFERENCE EXAMPLE 6

Preparation of 2-chloro-4-(4-fluorophenyl)quinoline

A mixture of 12 g of 4-(4-fluorophenyl)carbostyril and 50 ml of phosphorus oxychloride is heated under reflux for 1.5 hours and then concentrated under reduced pressure. Ice-water is added to the residue and the resulting mixture is extracted with chloroform. The organic layer is dried over anhydrous sodium sulfate and concentrated under reduced pressure. The residue is recrystallized from diethyl ether - ethanol to give 11.1 g of the title compound, m.p. 118° C.

REFERENCE EXAMPLES 7 to 10

The following compounds are prepared in substantially the same manner as in Reference Example 6 using the corresponding starting materials and recrystallized from the solvent designated in parentheses after the indication of melting points;

2-chloro-4-(4-chlorophenyl)quinoline, m.p. 148° C. (chloroform - hexane);

2-chloro-4-(4-methylphenyl)quinoline, m.p. 78°–79° C. (diethyl ether - hexane);

2-chloro-4-(4-trifluoromethylphenyl)quinoline, m.p. 138°–139° C. (chloroform - hexane); and 2-chloro-4-(3-trifluoromethylphenyl)quinoline, m.p. 118°–120° C. (chloroform - hexane).

REFERENCE EXAMPLES 11 to 13

The following compounds are prepared in substantially the same manner as in Example 3 using the corresponding starting materials and recrystallized from the solvent designated in parentheses after the indication of melting points:

2-(1-piperazinyl)-4-(4-fluorophenyl)quinoline ¼ hydrate, m.p. 139° C. (chloroform - diethyl ether);

2-(1-piperazinyl)-4-(4-methylphenyl)quinoline dimaleate ¼ hydrate, m.p. 168°–169° C. (methanol - ethyl acetate); and 2-(1-piperazinyl)-4-(4-trifluoromethylphenyl)quinoline dimaleate, m.p. 184°–185° C. (methanol - ethyl acetate).

EXAMPLE 16

| Tablets | |
|---|---|
| 2-[4-(2-Hydroxyethyl)-1-piperazinyl]-4-(4-fluorophenyl)quinoline dihydrochloride | 10 g |
| Corn starch | 33 g |
| Lactose | 70 g |
| Microcrystalline cellulose | 30 g |
| Hydroxypropylcellulose | 5 g |
| Light anhydrous silicic acid | 1 g |
| Magnesium stearate | 1 g |

The above components are blended, granulated and made into 1,000 tablets each weighing 150 mg by a conventional method. The tablets are further coated with hydroxypropyl methylcellulose, talc, titanium dioxode, and sorbitan monooleate in a customary manner. There are obtained 1,000 film coated tablets.

EXAMPLE 17

| Capsules | |
|---|---|
| 2-(4-Ethyl-1-piperazinyl)-4-(4-chlorophenyl)quinoline dimaleate | 20 g |
| Corn starch | 42 g |
| Lactose | 10 g |
| Microcrystalline cellulose | 25 g |
| Hydroxypropylcellulose | 2 g |
| Light anhydrous silicic acid | 0.5 g |
| Magnesium stearate | 0.5 g |

The above components are blended, granulated and filled into 1,000 capsules by a conventional method.

EXAMPLE 18

| Fine granules | |
|---|---|
| 2-(1-Piperazinyl)-4-(4-chlorophenyl)-quinoline maleate | 100 g |
| Corn starch | 200 g |
| Lactose | 660 g |
| Light anhydrous silicic acid | 10 g |
| Hydroxypropylcellulose | 30 g |

The above components are blended and made into fine granules by a conventional method. The fine granules are further coated with dimethylaminoethyl acrylatemethacrylate copolymer, macrogol, titanium dioxide, talc and magnesium stearate in a customary manner.

Industrial Applicability

The compounds of the formula (I) and pharmaceutically acceptable salts thereof are useful as an antiulcer agent and a therapeutic agent for inflammatory gastrointestinal diseases. They can be used in the prophylaxis and treatment of peptic ulcer and inflammatory gastrointestinal diseases in mammals including human.

What is claimed is:

1. A method for inhibiting and/or treatment of peptic ulcer in mammals which comprises administering to said mammals in need of such inhibiting and/or treatment an effective amount of a compound selected from the group consisting of 2[4-(2-hydroxyethyl)-1-piperazinyl]-4-(4-fluorophenyl)quinoline, 2-[4-(3-hydroxypropyl)-1-piperazinyl]-4-(4-fluorphyeny)-quinoline, 2-(1-piperazinyl)-4-(4-chlorophenyl)quinoline, 2-(4-ethyl-1-piperazinyl)-4-(4-chlorophenyl)quinoline, 2-[4-(2-hydroxyethyl)-1-piperazinyl]-(4-(4-methylphenyl)quinoline, and 2-[4-(2-hydroxyethyl)-1-piperazinyl]-4-(4-trifluoromethylphenyl)quinoline, or a pharmaceutically acceptable salt thereof.

2. The method according to claim 1, wherein said compound is 2-[4-(2hydroxyethyl-1-piperazinyl)]-4-(4-fluorophenyl)quinoline, or a pharmaceutically acceptable salt thereof.

3. The method according to claim 1 wherein said compound is administered in a daily dosage of from 0.1 to 20 mg per kg of body weight.

4. The method according to claim 2, wherein said compound is administered in a daily dosage of from 0.1 to 20 mg per kg of body weight.

5. The method acccording to claim 3, wherein said daily dosage is in the range of from 0.2 to 10 mg per kg of body weight.

6. The method according to claim 4, wherein said daily dosages is in the range of from 0.2 to 10 mg per kg of body weight.

* * * * *